United States Patent [19]

Bosies et al.

[11] Patent Number: 5,366,969
[45] Date of Patent: Nov. 22, 1994

[54] AMIDINE GROUP CONTAINING MONOCYCLOHETERACYCLIC OR BICYCLOHETEROCYCLIC DIPHOSPHONIC ACID DERIVATIVES AND MEDICAMENTS CONTAINING THESE COMPOUNDS

[75] Inventors: Elmar Bosies, Weinheim; Harald Zilch, Mannheim, both of Germany

[73] Assignee: Boehringer Mannheim GmbH, Mannheim, Germany

[21] Appl. No.: 829,019

[22] PCT Filed: Sep. 1, 1990

[86] PCT. No.: PCT/EP90/01469

§ 371 Date: Mar. 6, 1992

§ 102(e) Date: Mar. 6, 1992

[87] PCT Pub. No.: WO91/03481

PCT Pub. Date: Mar. 21, 1991

[30] Foreign Application Priority Data

Sep. 9, 1989 [DE] Germany ............................ 3930130

[51] Int. Cl.$^5$ ...................... A61K 31/66; C07F 9/38; C07F 9/40
[52] U.S. Cl. .................................. 514/81; 514/80; 514/84; 514/212; 544/242; 544/243; 544/244; 544/281; 540/542
[58] Field of Search ................. 544/281, 244, 552, 57, 544/122, 243, 244, 281; 514/80, 81, 86; 540/542

[56] References Cited

U.S. PATENT DOCUMENTS

| | | | |
|---|---|---|---|
| 3,761,479 | 9/1973 | Hoffman et al. | 544/244 |
| 3,857,838 | 12/1974 | Perronnet et al. | 544/244 |
| 4,345,078 | 8/1982 | Hofer et al. | 544/244 |
| 4,971,958 | 11/1990 | Bosies et al. | 514/89 |

Primary Examiner—Mukund J. Shah
Assistant Examiner—P. K. Sripada
Attorney, Agent, or Firm—Nikaido Marmelstein Murray & Oram

[57] ABSTRACT

Compounds of the formula I

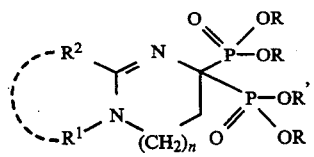

in which R can be hydrogen or $C_1$–$C_4$-alkyl, $R^1$ hydrogen, $C_1$–$C_6$-alkyl, aryl, aryl-$C_1$–$C_4$-alkyl, amino-$C_1$–$C_6$-alkyl, $C_1$–$C_6$-alkylamino-$C_1$–$C_4$-alkyl, $C_1$–$C_6$-dialkylamino-$C_1$–$C_4$-alkyl, $C_1$–$C_4$-alkoxy-$C_1$–$C_4$-alkyl, $C_1$–$C_4$-alkylthio-$C_1$–$C_4$-alkyl, $C_3$–$C_7$-alkenyl, $R^2$ $R^1$ or $C_2$–$C_7$-alkenyl, $C_1$–$C_6$-alkylmercapto, $C_1$–$C_6$-alkoxy, phenoxy-$C_1$–$C_4$-alkyl,amino, $C_1$–$C_4$-alkylamino, di-$C_1$–$C_4$-alkylamino, morpholino, thiomorpholino, pyrrolidino, piperidino, hexamethyleneimino, pyrasolino, imidazolino, n 0, 1 or 2 and $R^1$ and $R^2$, together with the carbon and the nitrogen atom to which they are attached, can form a heterocyclic five-, six- or seven-membered ring with 1-4 heteroatoms, whereby the heteroatoms can be the same or different and signify oxygen, nitrogen or sulphur and the annelated ring can possibly be substituted by one or more $C_1$–$C_6$-alkyl, $C_1$–$C_6$-alkoxy, $C_1$–$C_6$-alkylmercapto groups, hydroxyl, amino, nitro, halogen or halomethyl, as well as their pharmacologically acceptable salts, processes for their preparation, as well as medicaments which contain these compounds for the treatment of calcium metabolism disturbances.

9 Claims, No Drawings

AMIDINE GROUP CONTAINING MONOCYCLOHETERACYCLIC OR BICYCLOHETEROCYCLIC DIPHOSPHONIC ACID DERIVATIVES AND MEDICAMENTS CONTAINING THESE COMPOUNDS

The present invention concerns new amidine group-containing diphosphonic acid derivatives, processes for their preparation, as well as medicaments which contain these substances.

In DE 18 13 659 are described diphosphonic acid derivatives of which 1-hydroxyethane-1,1-diphosphonic acid has achieved importance for the treatment of Paget's disease.

EP 282 320-A-1 describes substituted 3-isoxazolylaminomethylenediphosphonic acids and their esters with anti-hypercalcaemic and anti-arthritic action.

In EP 282 309-A-2 are described "azol"-aminomethylenediphosphonic acids as hypercalcaemia inhibitors.

Furthermore, one knows from JP 63/150 290-A-2 aminomethylenediphosphonic acids as regulators of the calcium metabolism and from EP 274 158-A-1 tetrahydropyrimidinyl- and tetrahydropyridylaminomethylenediphosphonic acids for the treatment of an abnormal calcium and phosphate metabolism.

In the Patent Specifications U.S. Pat. No. 4,447,256, JP 55/89 210, JP 55/98 104, JP 55/98 105, JP 55/94 307 and JP 55/94 309 are described, inter alia, pyridylaminomethylenephosphonic acids as herbicides.

Amidine group-containing geminal diphosphonic acids with only one nitrogen in the ring, to which the two phosphonic acids are bound, are known from DE 3 208 600-A-1 and Lieoigs Ann. Chem. 1982, 275.

It has now been found that analogous derivatives of these compounds with an amidine structure in the ring are also very good calcium complex formers but, in addition, also show an excellent action on the calcium metabolism and thus are suitable for the broad treatment of calcium metabolism disturbances. In particular, they can be very well used where the bone build-up and breakdown is disturbed, i.e. they are suitable for the treatment of diseases of the skeletal system, such as e.g. osteoporosis, Paget's disease, Bechterew's disease and the like.

However, on the basis of these properties, they also find use in the therapy of bone metastases, of urolithiasis and for the prevention of heterotopic ossifications. Furthermore, due to their influencing of the calcium metabolism, they form a basis for the treatment of rheumatoid arthritis, of osteoarthritis and of degenerative arthrosis.

Accordingly, the subject of the present invention are diphosphonates of the general formula I

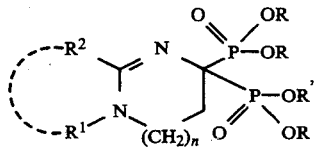

in which R can be hydrogen or $C_1$-$C_4$-alkyl, $R^1$ hydrogen, $C_1$-$C_6$-alkyl, aryl, aryl-$C_1$-$C_4$-alkyl, amino-$C_1$-$C_6$-alkyl, $C_1$-$C_6$-alkylamino-$C_1$-$C_4$-alkyl, $C_1$-$C_6$-dialkylamino-$C_1$-$C_4$-alkyl, $C_1$-$C_4$-alkoxy-$C_1$-$C_4$-alkyl, $C_1$-$C_4$-alkylthio-$C_1$-$C_4$-alkyl, $C_3$-$C_7$-alkenyl, $R^2$ $R^1$ or $C_2$-$C_7$-alkenyl, $C_1$-$C_6$-alkylmercapto, $C_1$-$C_6$-alkoxy, phenoxy-$C_1$-$C_4$-alkyl, amino, $C_1$-$C_4$-alkylamino, di-$C_1$-$C_4$-alkylamino, morpholino, thiomorpholino, pyrrolidino, piperidino, hexamethyleneimino, pyrazolino, imidazolino, n 0, 1 or 2 and $R^1$ and $R^2$, together with the carbon and the nitrogen atom to which they are bound, can form a heterocyclic five-, six- or seven-membered ring with 1-4 heteroatoms, whereby the heteroatoms can be the same or different and signify oxygen, nitrogen or sulphur, and the annelated ring can possibly be substituted by one or more $C_1$-$C_6$-alkyl, $C_1$-$C_6$-alkoxy, $C_1$-$C_6$-alkylmercapto groups, hydroxyl, amino, nitro, halogen or halomethyl, as well as their pharmacologically acceptable salts.

For the case that $R^1$ and $R^2$, together with the carbon and the nitrogen atom to which they are attached, form a heterocyclic ring, it is thereby preferably a question of the annelated pyrroline, pyrazoline, imidazoline, triazoline, oxazoline, isoxazoline, thiazoline, isothoazoline, thiadiazoline, oxadiazoline, pyridine, pyrimidine, pyrazine, pyridazine, oxazine, thiazine, triazine, tetrazine, diazepine, azacycloheptane, -heptene, -heptadiene, oxaazacycloheptane, -heptene, -heptadiene, thiaazacycloheptane, -heptene or heptadiene ring. The annelated heterocycles can be hydrogenated or contain up to two double bonds.

Alkyl, alkoxy, alkylamino and alkylmercapto substituents in the radicals $R^1$ and $R^2$ can be straight-chained or branched and contain 1-6, preferably 1-4 carbon atoms. Preferred is the methyl, ethyl, isopropyl, methoxy, ethoxy, methylamino, ethylamino, methylmercapto and ethylmercapto radical.

By aryl is preferably to be understood the phenyl radical. Halogen stands, in general, for fluorine, chlorine and bromine, preferably fluorine and chlorine.

R is preferably to represent hydrogen.

The preferred alkenyl radical is the allyl or butenyl radical, dialkylamino preferably stands for dimethyl- and diethylamino and the straight-chained or branched alkylene chain of the arylalkyl, phenoxyalkyl, alkoxyalkyl, alkylthioalkyl, alkylaminoalkyl radicals, preferably represents the methylene, ethylene, isopropylene chain. The corresponding $C_1$-$C_4$-alkyl parts of the stated substituents preferably stand for methyl and ethyl.

In the case of the monocyclic compounds of the gen. formula I, it is preferably a question of substituted 5,6-dihydro-1H-pyrimidine-4,4-diphosphonic acids and 1,3-diaza-2-cycloheptene-4,4-diphosphonic acids of the formula I. Preferred bicyclic compounds of the general formula I are the pyridopyrimidine, pyrimidopyrimidine, oxazolopyrimidine, thiazolopyrimidine, triazolopyrimidine, oxadiazolopyrimidine, thiadiazolopyrimidine, imidazopyrimidine, pyrimidothiazine, pyridodiazepin, oxazilodiazepine, thiazolodiazepine and pyrrolopyrimidine ring system.

n is preferably 1 or 2.

Especially preferred bicycles are the pyrido-(1,2-a)-pyrimidine-, oxazolo-(3,2-a)-pyrimidine-, thiazolo-(3,2-a)-pyrimidine-, 1,2,4-triazolo-(1,5-a)-pyrimidine-, pyrimido-(1,2-a)-pyrimidine-pyrimido-(2,1-b)-1,3-thiazine-and pyrimido-(1,2-a)-1,3-diazepine-diphosphonic acids.

The compounds can be present as stereoisomeric mixtures or as pure cis- or trans-isomers.

Asymmetric carbon atoms can possess the R- or S-configuration and the compounds can be present optically-active or as racemates.

The compounds of the gen. formula I are prepared according to per se known processes, preferably in that one reacts a pyrimidinone of the general formula II

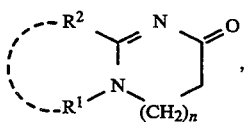

in which $R^1$, $R^2$ and n have the above-given meaning, with a mixture of phosphorous or phosphoric acid and a phosphorus halide or phosphoryl halide, or one can also bring the phosphorus halide to reaction alone in the presence of water and subsequently hydrolyses to the free diphosphonic acid or, if desired, converts the isolated compounds of the general formula I into their esters or into pharmacologically acceptable salts.

The pyrimidinones of the gen. formula II used in the preparation process are brought to reaction with 1–5, preferably 2–3 mol of phosphorous acid or phosphoric acid and 1–5, preferably 2–3 mol of phosphoryl halide, phosphorus trihalide or phosphorus pentahalide and at 80°–130° C., preferably 100° C. In the case of the phosphorus or phosphoryl halides, it is preferably a question of the chloride or bromides. One can also carry out the reaction in the presence of dilution agents, such as halogenated hydrocarbons, especially chlorobenzene, tetrachloroethane, or also dioxane, possibly with the addition of water. The subsequent hydrolysis takes place by heating with water but expediently with half concentrated hydrochloric or hydrobromic acid.

The free diphosphonic acids of the general formula I can be converted by heating with orthoformic acid alkyl esters into the corresponding tetralkyl esters and to diesters or again saponified to the free tetraacids. As a rule, the saponification to diesters takes place in that one treats the tetraalkyl esters with an alkali metal halide, preferably sodium iodide, in a suitable solvent, such as e.g. acetone, at room temperature.

There hereby results the symmetrical diester/-disodium salt which can possibly be converted by an acidic ion exchanger into the diester/diacid. The saponification of the esters to free diphosphonic acids takes place, as a rule, by boiling with hydrochloric or hydrobromic acid. However, one can also carrying out a cleavage with trimethylsilyl halide, preferably the bromide or iodide.

Compounds of the general formula I can also be subsequently converted into other compounds of the general formula I. This concerns e.g. the hydrogenation of unsaturated substituents to the corresponding aliphatic radicals or the partial or complete hydrogenation of double bonds in mono- and bicyclic compounds.

Furthermore, by splitting off of protective groups, compounds of the general formula I can be converted into other compounds of the formula I.

As pharmacologically acceptable salts, there are, above all, used mono- and dialkali metal or ammonium salts which are prepared in the usual way, e.g. by titration of the compounds with inorganic or organic bases, such as e.g. sodium or potassium hydrogen carbonate, aqueous sodium hydroxide solution, aqueous potassium hydroxide solution, aqueous ammonia or amines, such as e.g. trimethyl-, triethyl- or cyclohexylamine.

As a rule, the salts are purified by reprecipitation from water/methanol or water/acetone.

The new substances of the formula I according to the invention and their salts can be administered enterally or parenterally in liquid or solid form. There hereby come into question all usual forms of administration, for example tablets, capsules, dragees, syrups, solutions, suspensions etc. As injection medium, water is preferably used which contains the additives usual in the case of injection solutions, such as stabilising agents, solubilising agents and buffers.

Such additives are e.g. tartrate and citrate buffers, ethanol, complex formers (such as ethylenediamine-tetreactic acid and its non-toxic salts), high molecular polymers (such as liquid polyethylene oxide) for viscosity regulation. Liquid carrier materials for injection solutions must be sterile and are preferably filled into ampoules. Solid carrier materials are e.g. starch, lactose, mannitol, methyl cellulose, talc, highly dispersed silicic acids, high molecular fatty acids (such as stearic acid), gelatine, agar-agar, calcium phosphate, magnesium stearate, animal and vegetable fats, solid high molecular polymers (such as polyethylene glycols); compositions suitable for oral administration can, if desired, contain flavouring and sweetening materials.

The dosaging can depend upon various factors, such as mode of administration, species, age and/or individual state of health. The doses to be administered daily lie at about 1–1000 mg/human, preferably 10–200 mg/human and can be taken all at once or divided up several times.

Preferred in the meaning of the present invention are, apart from the compounds mentioned in the Examples and compounds derivable by combination of all meanings of the substituents mentioned in the claims, the following diphosphonic acids, as well as their sodium salts, methyl or ethyl esters: 5,6-dihydro-1H-pyrimidine-4,4-diphosphonic acid 1-methyl-5,6-dihydro-1H-pyrimidine-4,4-diphosphonic acid
2-dimethylamino-1-methyl-5,6-dihydro-1H-pyrimidine-4,4-diphosphonic acid
2-phenyl-5,6-dihydro-1H-pyrimidine-4,4-diphosphonic acid
1,2-dimethyl-5,6-dihydro-1H-pyrimidine-4,4-diphosphonic acid
2-ethoxy-1-methyl-5,6-dihydro-1H-pyrimidine-4,4-diphosphonic acid
2-ethylmercapto-1-methyl-5,6-dihydro-1H-pyrimidine-4,4-diphosphonic acid
1,2-dimethyl-1,3-diaze-2-cycloheptane-4,4-diphosphonic acid
2-methyl-1,3-diaza-2-cycloheptene-4,4-diphosphonic acid
2-amino-1,3-diaza-2-cycloheptane-4,4-diphosphonic acid
2-ethoxy-1-methyl-1,3-diaza-2-cycloheptene-4,4-diphosphonic acid
2-ethylmercapto-1-methyl-1,3-diaza-2-cycloheptene-4,4-diphosphonic acid
2,3,4,5-tetrahydropyrido-(1,2-a)-1,3-diazepine-2,2-diphosphonic acid
2,3,4,5,7,8,9,10-octahydropyrido-(1,2-a)-1,3-diazepine-2,2-diphosphonic acid
8-chloro-2,3,4,5,7,8,9,10-octahydropyrido-(1,2-a)-1,3-diazepine-2,2-diphosphonic acid
3,4,6,7-tetrahydro-2H,8H-pyrimido-(2,1-b)-1,3-thiazine-8,8-diphosphonic acid
3-methyl-5,6-dihydro-7H-thiazolo-(3,2-a)-pyrimidine-7,7-diphosphonic acid
3-methyl-2,3,5,6-tetrahydro-7H-thiazolo-(3,2-a)-pyrimidine-7,7-diphosphonic acid 3-methyl-2,3,5,6-tetrahydro-7H-oxazolo-(3,2-a)-pyrimidine-7,7-diphosphonic acid 7-chloro-3,4-dihydro-2H-pyrido-(1,2-a)-pyrimidine-2,2-diphosphonic acid
7-methyl-3,4,6,7,8,9-hexahydro-2H-pyrido-(1,2-a)-pyrimidine-2,2-diphosphonic acid
3,4,7,8-tetrahydro-6H-pyrrolo-(1,2-a)-pyrimidine-2,2-diphosphonic acid
2,3,5,6-tetrahydro-1H-imidazo-(1,2-a)-pyrimidine7,7-diphosphonic acid
3,4,6,7,8,9-hexahydro-2H-pyrimido-(1,2-a)-pyrimidine2,2-diphosphonic acid
6,7-dihydro-1,2,4-triazolo-(1H)-(1,5-a)-pyrimidine-5,5-diphosphonic acid The following Examples show some of the process variants which can be used for the synthesis of the compounds according to the invention. However, they are not to represent a limitation of the subject of the invention. As a rule, the compounds are obtained as high-melting solid products (mono- or disodium salts), the structure of which is verified by $^1$H—, —p— and possibly by $^{13}$C—NMR spectroscopy. The purity of the substances were determined by means of C, H, N, P, S, Na analysis, as well as by thin layer electrophoresis (cellulose, oxalate buffer of pH=4.0). For the characterisation of the individual compounds, there are given the $M_{rel}$ values (=relative mobility) referred to pyrophosphate ($M_{rel}=1$).

The pyrimidinones of the general formula II used as starting compounds are prepared according to known processes, e.g. in that one brings substituted acyclic or cyclic amidines or guanidines to reaction with acrylic acid esters, acrylic acid halides or 3-bromopropionic acid halides.

The educts needed for the Examples, insofar as they were not commercially available, were synthesised in analogy to the following literature references: Liebigs Ann. Chem. 1974, 593; Chem. Ber. 104, 3961(1971)); Chem. Pharm. Bull. 19, 764 (1971); Chem. Pharm. Bull. 20, 901 (1972); Monatsh. Chem. 116, 237 (1985).

EXAMPLE 1

3,4-Dihydro-2H-pyrido-(1,2-a)-pyrimidine-2,2-diphosphonic acid 5 g 3,4-Dihydropyrido-(1,2-a)-pyrimidin-2-one (Fluka) were melted at 80° C. with 5.5 g H$_3$PO$_4$ and mixed, while stirring, with 5.9 ml PCl$_3$. After 20 hours at the given temperature, it was mixed with 70 ml 2N HCl, stirred for 8 hours at 100° C. and, after cooling, filtered off from the undissolved part. The filtrate was evaporated on a rotary evaporator and purified by ion exchanger chromatography on Amberlite IR 120 (H+ form) with water as eluent. The fractions obtained after electrophoresis were evaporated in a vacuum and the oil remaining behind, after dissolving in a little water, brought to crystallisation by the addition of acetone.

$M_{rel}$ 0.33, yield 3.8 g (38% of theory); m.p. 300°–304° C.

EXAMPLE 2

3,4,6,7,8,9-Hexahydro-2H-pyrido-(1,2-a)-pyrimidine-2,2-diphosphonic acid 3 g of the diphosphonic acid obtained in Example 1 were dissolved in 250 ml water and, after addition of 1.5 g PtO$_2$, hydrogenated at atmospheric pressure up to the take-up of the calculated amount of hydrogen. After separation off of the catalyst and evaporation in a vacuum, the residue was brought to crystallisation from water/acetone. $M_{rel}$ 0.33, yield 2.61 g (85% of theory), m.p. 279°–285° C. (decomp.).

EXAMPLE 3

2,3,5,6-Tetrahydro-7H-oxazolo-(3,2-a)-pyrimidine-7,7-diphosphonic acid 5.7 g 2,3,5,6-tetrahydro-7H-oxazolo-(3,2-a)-pyrimidin-7-one (m.p. 146°–147° C.) were melted at 60° C. with 6.7 g H$_3$PO$_4$, slowly mixed, while stirring, with 7.5 ml POCl$_3$ and kept at 60° C. for 36 hours. The excess POCl$_3$ was then stripped off in a vacuum, the residue mixed with 80 ml water and the clear solution heated for 1 hour to 100° C. After cooling, it was worked up and purified as described in Example 1. $M_{rel}$ 0.42, yield 1.4 g (12% of theory), m.p. 145° C. (decomp.).

EXAMPLE 4

6,7-Dihydro-(1H)-1,2,4-triazolo-(1,5-a)-pyrimidine-5,5-diphosphonic acid 2 g 6,7-dihydro-(1H)-1,2,4-triazolo-(1,5-a)-pyrimidin-5-one (m.p. 237°–239° C.) were brought to reaction analogously to Example 3 for 8 hours at 80° C. and hydrolysed for 3 hours at 100° C. The working up and purification also took place with reference to Examples 1 and 3. $M_{rel}$ 0.39, yield 0.95 g (23% of theory), m.p. 167°–171° C. (decomp.).

EXAMPLE 5

3,4-Dihydro-2H-pyrimido-(1,2-a)-pyrimidine-2,2-diphosphonic acid 1.5 g 3,4-dihydro-2H-pyrimido-(1,2-a)-pyrimidin-2-one (m.p. 263° C.) were reacted analogously to Example 4. $M_{rel}$ 0.6, yield 0.82 g (28% of theory), m.p.>85° C. (decomp.).

EXAMPLE 6

2-Methyl-5,6-dihydro-1H-pyrimidine-4,4-diphosphonic acid 5 g 2-methyl-5,6-dihydro-1H-pyrimidin-4-one (m.p. 123°–125° C.) were reacted with reference to Examples 1, 3 and 4. $M_{rel}$ 0.31, yield 1.28 g (14% of theory), m.p.>101° C. (decomp.).

EXAMPLE 7

2-Amino-1-methyl-5,6-dihydro-1H-pyrimidine-4,4-diphosphonic acid 1.2 g 2-amino-1-methyl-5,6-dihydro-1H-pyrimidin-4-one (m.p. 255°–257° C.) were reacted with reference to Examples 1, 3, 4 and 6. $M_{rel}$ 0.32, yield 0.6 g (23% of theory), m.p. 308° C.

We claim:

1. Compound of formula I:

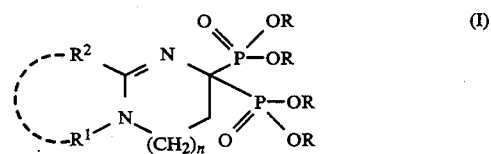

wherein

R is hydrogen or C$_1$–C$_4$-alkyl, R$^1$ is hydrogen, C$_1$–C$_6$-alkyl, aryl, aryl-C$_1$–C$_4$-alkyl, amino-C$_1$–C$_6$-alkyl, C$_1$–C$_6$-alkylamino-C$_1$–C$_4$-alkyl, di-C$_1$–C$_6$ alkylamino-C$_1$–C$_4$-alkyl, C$_1$–C$_4$-alkoxy-C$_1$–C$_4$-alkyl, C$_1$–C$_4$-alkylthio-C$_1$–C$_4$-alkyl, or C$_3$–C$_7$-alkenyl; $R^2$ is $R^1$ or $C_1$–$C_7$-alkenyl, $C_1$–$C_6$-alkylmercapto, $C_1$–$C_6$-alkoxy, phenoxy-$C_1$–$C_4$-alkyl, amino, $C_1$–$C_4$-alkylamino, di-$C_1$–$C_4$-alkylamino, morpholino, thiomorpholino, pyrrolidino, piperidino, hexamethyleneimino, pyrazolino, or imidazolino; or $R^1$ and $R^2$, together with carbon and the nitrogen atoms to which they are attached, form a heterocyclic ring selected from the group consisting of pyrroline, pyrazoline, imidazoline, triazoline, oxazoline, isoxazoline, thiazoline, isothiazoline, thiadiazoline, oxadiazoline, pyridine, pyrimidine, pyrazine, pyridazine, oxazine, thiazine, triazine, tetrazine, diazepine, azacycloheptane, azacycloheptene, azacycloheptadiene, oxaazacycloheptane, oxaazacycloheptene, oxaazacycloheptadiene, thiaazacycloheptane, thiaazacycloheptene and thiaazacycloheptadiene; and the annelated ring is optionally substituted by at least one of $C_1$–$C_6$-alkyl, $C_1$–$C_6$-alkoxy, $C_1$–$C_6$-alkyl-mercapto, hydroxyl, amino, nitro, halogen or halomethyl; and; n is 1;

and a pharmacologically acceptable salt thereof.

2. Compound of claim 1, wherein aryl is phenyl or naphthyl.

3. Compound of claim 1, wherein the compound is a monocyclic compound which is an optionally substituted 5,6-dihydro-1H-pyrimidine-4,4-diphosphonic acid.

4. Compound of claim 1, wherein the compound is a bicyclic compound selected form the group consisting of pyridopyrimidine, pyrimidopyrimidine, oxazolopyrimidine, thiazolopyrimidine, triazolopyrimidine, oxadiazolopyrimidine, thiadiazolopyrimidine, imidazopyrimidine, pyrimidothiazine, and pyrrolopyrimidine.

5. Compound of claim 4, wherein the bicyclic compound is selected from the group consisting of pyrido-(1,2-a)-pyrimidine-, diphosphonic acid, oxazolo-(3,2-a)-pyrimidine-, thiazolo-(3,2-a)-pyrimidine-diphosphonic acid, 1,2,4-triazolo-(1,5-a)-pyrimidine-diphosphonic acid, pyrimido-(1, 2-a)-pyrimidine-diphosphonic acid and pyrimido-(2,1-b)-1,3-thiazine-diphosphonic acid.

6. Compound of claim 1, wherein said compound is
3,4-dihydro-2H-pyrido-(1,2-a)-pyrimidine-2,2-diphosphonic acid;
3,4,6,7,8,9-hexahydro-2H-pyrido-(1,2-a)-pyrimidine-2,2-diphosphonic acid;
2,3,5,6-tetrahydro-7H-oxazolo-(3,2-a)-pyrimidine-7,7-diphosphonic acid;
6,7-dihydro-(1H)-1,2,4-triazolo-(1,5-a)-pyrimidine-5,5-diphosphonic acid;
3,4-dihydro-2H-pyrimido-(1,2-a)-pyrimidine-2,2-diphosphonic acid;
2-methyl-5,6-dihydro-1H-pyrimidine-4,4-diphosphonic acid; or
2-amino-1-methyl-5,6-dihydro-1H-pyrimidine-4,4-diphosphonic acid.

7. Pharmaceutical composition for the treatment of calcium metabolism disturbances comprising a calcium metabolism disturbance treating effective amount of compound of claim 1 and a pharmaceutically acceptable carrier therefor.

8. A method of treating a calcium metabolism disturbance in a patient in need of such treatment, said method comprising administering to said patient a calcium metabolism disturbance treating effective amount of a compound of claim 1.

9. Method of claim 8, wherein the calcium metabolism disturbance is osteoporosis.

* * * * *